(12) United States Patent
Tomohira

(10) Patent No.: US 8,703,189 B2
(45) Date of Patent: *Apr. 22, 2014

(54) MEDICINAL COMPOSITION

(75) Inventor: Yuso Tomohira, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 407 days.

This patent is subject to a terminal disclaimer.

(21) Appl. No.: 10/477,427

(22) PCT Filed: May 23, 2002

(86) PCT No.: PCT/JP02/04979
§ 371 (c)(1),
(2), (4) Date: Nov. 13, 2003

(87) PCT Pub. No.: WO02/096466
PCT Pub. Date: Dec. 5, 2002

(65) Prior Publication Data
US 2004/0175422 A1    Sep. 9, 2004

(30) Foreign Application Priority Data

May 25, 2001 (JP) ................................. 2001-156815
Oct. 17, 2001 (JP) ................................. 2001-319075

(51) Int. Cl.
*A61K 9/22* (2006.01)
*A61K 9/26* (2006.01)
*A61K 9/14* (2006.01)
*A61K 9/50* (2006.01)

(52) U.S. Cl.
USPC ........... 424/468; 424/469; 424/489; 424/502; 514/263.34

(58) Field of Classification Search
USPC ....................................................... 424/486
See application file for complete search history.

(56) References Cited

U.S. PATENT DOCUMENTS

| | | | | |
|---|---|---|---|---|
| 5,399,357 A | * | 3/1995 | Akiyama et al. | 424/457 |
| 5,494,681 A | * | 2/1996 | Cuca et al. | 424/484 |
| 5,952,005 A | * | 9/1999 | Olsson et al. | 424/458 |
| 6,030,644 A | * | 2/2000 | Nakagami et al. | 424/489 |
| 6,254,889 B1 | * | 7/2001 | Kigoshi et al. | 424/487 |

FOREIGN PATENT DOCUMENTS

| | | | |
|---|---|---|---|
| CA | 2270975 | 4/2003 | |
| EP | 368247 | 5/1990 | |
| EP | 368247 A2 * | 5/1990 | ............... A61K 9/16 |
| EP | 0841062 A1 | 5/1998 | |
| EP | 1025848 A1 | 8/2000 | |
| JP | 6-91150 | 4/1994 | |
| JP | 07-076517 | 3/1995 | |
| JP | 08-143450 | 6/1996 | |
| JP | 2000-169364 | 6/2000 | |
| WO | WO 94/12157 | 6/1994 | |
| WO | WO 96/14058 A1 | 5/1996 | |
| WO | WO 98/42323 | 10/1998 | |
| WO | 99/29299 A1 | 6/1999 | |
| WO | WO 00/18372 | 4/2000 | |
| WO | 00/74654 A1 | 12/2000 | |

OTHER PUBLICATIONS

Kojima et al., Development of controlled release matrix pellets by annealing with micronized water-insoluble or enteric polymers (J. of Controlled Release, 2002).*
Akiyama et al, *J. of Pharm. Sciences*, 83(11):1600-1607 (1994).
Lin, et al., "Bioavailability Studies of Theohylline Ethylcellulose Microcapsules Prepared by Using Ethylene-Vinyl Acetate Copolymer as a Coacervation-Inducing Agent," Journal of Pharmaceutical Sciences, vol. 76, No. 3, 219-223, Mar. 1987.

* cited by examiner

*Primary Examiner* — Michael G Hartley
*Assistant Examiner* — Nabila Ebrahim
(74) *Attorney, Agent, or Firm* — Sughrue Mion, PLLC

(57) ABSTRACT

The present invention provides a medicinal composition that exhibits excellent storage stability and, even over long-term storage, little change in the release rate of the pharmacologically active substance contained therein. The medicinal composition of the invention prepared by dissolving or dispersing a pharmacologically active substance and a pH-independent water-insoluble polymer in a molten low-melting substance, and which can be prepared by spraying a liquid substance, obtained by dissolving or dispersing the pharmacologically active substance in a molten mixture comprising the low-melting substance and the pH-independent water-insoluble polymer, and then cooling the liquid substance.

5 Claims, 3 Drawing Sheets

MEDICINAL COMPOSITION

CROSS-REFERENCE TO RELATED APPLICATION

This application is a 371 of PCT/JP02/04979, filed May 23, 2002; the disclosure of which is incorporated herein by reference.

TECHNICAL FIELD

This invention relates to a medicinal composition.

BACKGROUND ART

Low-melting-point substances, for example, wax-like substances, glycerine esters of fatty acids, etc., are used in fields such as sustained-release preparations and preparations for masking bitterness.

For example, Japanese Unexamined Patent Publication No. 1995-76517 discloses a pharmaceutical preparation obtained by coating very small spherical particles produced by melting or dispersing a pharmacologically active substance that has an unpleasant taste in a molten wax-like substance, with a coating film formed from a hydrophobic substance and/or a water-insoluble polymer.

The above-mentioned publication only discloses pH dependent water-insoluble polymers such as the polymers soluble in gastric juice or enteric polymers, but nowhere discloses a pH-independent water-insoluble polymer. Furthermore, because the invention disclosed in the above-mentioned publication uses organic solvents to dissolve the water-insoluble polymer, it causes problems of adverse effects on workers' health, environmental pollution, residues in preparation, etc.

Japanese Unexamined Patent Publication No. 1996-143450 discloses a sustained-release preparation comprising a water-soluble pharmacologically active substance, a glycerine ester of a fatty acid and a water-insoluble substance. The sustained-release preparation is obtained by mixing a water-soluble pharmacologically active substance with a glycerine ester of a fatty acid, melting and granulating the mixture, adding a water-insoluble substance to the granulated substance, regranulating, and compressing the regranulated substance.

However, pharmaceutical preparations that use low-melting-point substances, such as wax-like substances, glycerine esters of fatty acids, etc., have the drawbacks of having low long-term stability and lowered release rate of pharmacologically active substances from pharmaceutical preparations that have been stored for a long time.

The above-described two publications nowhere disclose the release rate of pharmacologically active substance after preserving the pharmaceutical preparation over a long period of time.

DISCLOSURE OF THE INVENTION

An object of the present invention is to provide a pharmaceutical preparation that exhibits excellent storage stability and, even after being stored for a long time, little change in the release rate of the pharmacologically active substance contained therein.

In view of the above-mentioned problems, the present inventors conducted extensive research and found that a pharmaceutical preparation, prepared by melting a pH-independent water-insoluble polymer in a molten low-melting-point substance, melting or dispersing a pharmacologically active substance in the molten mixture, and spraying and cooling the resultant liquid substance, exhibited excellent storage stability and little tendency to change the release rate of the pharmacologically active substance even after long-term storage. The present invention is accomplished based on these findings.

1. A medicinal composition prepared by dissolving or dispersing a pharmacologically active substance and a pH-independent water-insoluble polymer in a molten low-melting-point substance.

2. A medicinal composition prepared by dissolving or dispersing a pharmacologically active substance in a molten mixture containing a low-melting-point substance and a pH-independent water-insoluble polymer.

3. A medicinal composition prepared by spraying a liquid substance obtained by dissolving or dispersing a pharmacologically active substance in a molten mixture containing a low-melting-point substance and a pH-independent water-insoluble polymer, and cooling the sprayed liquid substance.

4. A medicinal composition according to one of Items 1 to 3, which is used as a sustained-release preparation or a fast-release preparation.

5. A medicinal composition according to one of Items 1 to 4, wherein the low-melting-point substance is a pharmaceutically acceptable substance with a melting point of 40 to 120° C. that is water-insoluble or hardly dissolves in water.

6. A medicinal composition according to one of Items 1 to 4, wherein the low-melting-point substance is a single substance or a mixture of two or more substances selected from the group consisting of glycerine esters of fatty acids, propylene glycol esters of fatty acids, sorbitan esters of fatty acids, paraffin, micro crystalline wax, ceresin, hardened oil, Japan tallow, cacao butter, carnauba wax, beeswax, cetanol, stearyl alcohol, myristic acid, palmitic acid, stearic acid, titanium stearate and calcium oleate.

7. A medicinal composition according to one of Items 1 to 4, wherein the pH-independent water-insoluble polymer is a single substance or a mixture of two or more substances selected from the group consisting of ethylcellulose, aminoalkyl methacrylate copolymer RS, aminoalkyl methacrylate copolymer RL, cellulose acetate, cellulose acetate butyrate, and cellulose acetate propionate.

8. A medicinal composition according to one of Items 1 to 4, wherein the pharmacologically active substance is at least one member selected from the group consisting of theophylline, cilostazol, grepafloxacin, carteolol, procaterol, rebamipide and aripiprazole.

9. A medicinal composition according to one of Items 1 to 4, which contains the low-melting-point substance in the proportion of from 50 to $1 \times 10^5$ wt. % relative to the pharmacologically active substance.

10. A medicinal composition according to Item 9, which contains the pH-independent water-insoluble polymer in the proportion of from 0.5 to 60 wt. % relative to the low-melting-point substance.

11. A medicinal composition according to one of Items 1 to 4, which is composed of particles having an average particle diameter of about from 10 to 1400 μm.

12. A medicinal composition comprising a low-melting-point substance, a pH-independent water-insoluble polymer and a pharmacologically active substance, wherein the pH-independent water-insoluble polymer and the pharmacologically active substance are independently and uniformly dispersed in each particle of the low-melting-point substance in a molecular state or a fine-particle state.

13. A medicinal composition comprising a low-melting-point substance, a pH-independent water-insoluble polymer and a pharmacologically active substance, wherein the pharmacologically active substance is uniformly dispersed in a molecular state or a fine-particle state in each particle of either a mixture or a dispersed substance containing the low-melting-point substance and the pH-independent water-insoluble polymer.

14. A medicinal composition according to Item 12 or 13, which is used as a sustained-release preparation or a fast-release preparation.

15. A method for preparing a medicinal composition comprising the steps of:
  obtaining a molten mixture by dissolving (melting) or dispersing a pH-independent water-insoluble polymer in a molten low-melting-point substance;
  obtaining a liquid substance by dissolving or dispersing a pharmacologically active substance in the molten mixture; and
  obtaining particles by spraying and then cooling the liquid substance.

16. A method for preparing a medicinal composition according to Item 15, wherein the medicinal composition is a sustained-release preparation or a fast-release preparation.

The medicinal compositions of the present invention include sustained-release preparations and fast-release preparations. The types of preparation can be suitably selected depending on the targeted disease, kind of pharmaceutically active substance, etc.

There is no particular limit on the pharmacologically active substance contained in the medicinal composition of the present invention and a wide range of publicly known substances can be used. Examples of usable pharmacologically active substances include those generally used in pharmaceutical preparations, such as bronchial dilator, gastrointestinal drugs, circulatory drugs, central nerves system drugs, preparations for peripheral nerves, antibiotics, chemotherapeutics, antitumor agents, platelet aggregation inhibitors, anti-allergy agents and vitamin preparations. Specific examples include pharmacologically active substances generally used in various kinds of pharmaceutical preparations, such as antibiotics, antifungal agents, antilipemics, circulatory drugs, antiplatelets (platelet aggregation inhibitors), antitumor agents, antipyretics, analgesics, antiphlogistics, antitussive and expectorant agents, sedative agents, muscle relaxants, antiepileptic agents, antiulcer agents, antidepressants, anti-allergy agents, cardiotonics, antiarrhythmics, vasodilators, hypotensive diuretics, diabetic medicines, anticoagulants, hemostatic drugs, antituberculosis drugs, hormone drugs, narcotic antagonists, bone-resorption inhibitors, vascularization inhibitors, antipodagrics, etc. More specifically, theophylline, cilostazol, grepafloxacin, carteolol, procaterol, rebamipide, aripiprazole, etc., can be used.

As the low-melting-point substance(s), various pharmaceutically acceptable substances having a melting point of 40 to 120° C. that are water-insoluble or hardly dissolve in water can be used. Examples of usable substances include glycerine esters of fatty acids, propylene glycol esters of fatty acids, sorbitan esters of fatty acids, paraffin, micro crystalline wax, ceresin, hardened oil, Japan tallow, cacao butter, carnauba wax, beeswax, cetanol, stearyl alcohol, myristic acid, palmitic acid, stearic acid, titanium stearate and calcium oleate. These low-melting-point substances can be used singly or in combination of two or more types. Among the above-mentioned low-melting-point substances, glycerin fatty acid esters are preferable, and glycerin behenic acid esters and glycerin stearic acid esters are especially preferable.

When a pharmaceutically active substance has unpleasant taste (bitterness, etc.), by using the above-mentioned low-melting-point substance, the unpleasant taste of the pharmaceutically active substance can be masked and it can be readily formed into a powder, granules, dry-syrup, etc.

As a pH-independent water-insoluble polymer, various kinds of publicly known water-insoluble polymers that have pH-independent solubility can be used. Examples of usable polymers include ethylcellulose, aminoalkyl methacrylate copolymer RS (eudragit RS-100, eudragit RS-PO (manufactured by Rhom GmbH & Co.KG), etc.), aminoalkyl methacrylate copolymer RL (eudragit RL-100, eudragit RL-PO (manufactured by Rhom GmbH & Co.KG), etc.), cellulose acetate, cellulose acetate butyrate, cellulose acetate propionate, etc. These pH-independent water-insoluble polymers are used singly or in combination of two or more types. Among the above-mentioned pH-independent water-insoluble polymers, ethylcellulose, aminoalkyl methacrylate copolymer RS and aminoalkyl methacrylate copolymer RL are preferable. Ethylcellulose is the most preferable among them.

Particles obtained by spraying and cooling a molten mixture comprising a low-melting-point substance and a pharmacologically active substance usually exhibit blocking (aggregation) when they are left standing; however, when the abovementions pH-independent water-insoluble polymer is added thereto, blocking is prevented and they become easy to handle.

It is preferable that the low-melting-point substance be contained in the medicinal composition of the present invention generally from 50 to $1\times10^5$ wt. %, preferably from 75 to $3\times10^4$ wt. % and more preferably from 100 to $1\times10^4$ wt. %, based on the pharmacologically active substance.

It is preferable that the pH-independent water-insoluble polymer be contained in the medicinal composition of the present invention generally from 0.5 to 60 wt. %, preferably from 1 to 50 wt. % and more preferably from 2 to 45 wt. %, based on the low-melting-point substance.

The composition of the present invention is obtained by dissolving (melting) or dispersing a pH-independent water-insoluble polymer in a low-melting-point substance and dissolving or dispersing a pharmacologically active substance therein. The composition of the present invention can take the form of, for example, a powder, fine powders, dry-syrup, granules, tablets, capsules, etc.

The medicinal composition of the present invention (sustained-release preparation and fast-release preparation) can be prepared by, for example, the methods described below:
Method A:
  A low-melting-point substance is melted by heating, and a pharmacologically active substance and a pH-independent water-insoluble polymer are dissolved (melted) or dispersed in the molten substance to obtain a molten mixture. The molten mixture is sprayed and cooled to obtain particles. Using the obtained particles, the composition of the present invention taking the forms of a powder, fine powders, dry-syrup, etc., can be prepared.

The temperature at the time of melting the low-melting-point substance is set at or higher than the melting point of the low-melting-point substance, preferably higher than its melting point by 10° C. or more, provided the temperature does not adversely affect the stability of the pharmacologically active substance.

To uniformly dissolve (melt) or disperse the pH-independent water-insoluble polymer in the medicinal composition, the polymer is used in the form of a powder having an average particle diameter of generally about from 0.1 to 50 μm and preferably about from 0.5 to 20 μm.

To uniformly disperse the pharmacologically active substance in the medicinal composition, the pharmacologically active substance is used in the form of a power having an average particle diameter of generally about from 0.1 to 100 μm and preferably about from 0.5 to 50 μm.

There is no restriction on the order of adding the pharmacologically active substance and the pH-independent water-insoluble polymer to the molten substance comprising a low-melting-point substance. In other words, it is possible to dissolve or disperse a pharmacologically active substance in the molten substance and then dissolve (melt) or disperse a pH-independent water-insoluble polymer therein. It is also possible to dissolve (melt) or disperse a pH-independent water-insoluble polymer in the molten substance and then dissolve or disperse a pharmacologically active substance therein. Alternatively, dissolution or dispersion of a pharmacologically active substance and dissolution (melting) or dispersion of a pH-independent water-insoluble polymer in the molten substance can be conducted simultaneously.

The composition of the present invention that can take a form of a powder, fine powders, etc., is preferably prepared by the method comprising the steps of: melting a low-melting-point substance by heat; dissolving (melting) or dispersing a pH-independent water-insoluble polymer in the molten substance to obtain a molten mixture; further dissolving or dispersing a pharmacologically active substance in the molten mixture to obtain a liquid substance; spraying the liquid substance, and then cooling the sprayed liquid.

Spraying and cooling the liquid can be conducted by conventional methods employing a spray cooler using a rotary disc, a pressurized spray nozzle or a two fluid spray nozzle, etc. Cooling can generally be conducted at around room temperature. By suitably selecting the spray conditions, particles having a predetermined diameter can be obtained.

It is also possible to obtain particles having a predetermined diameter by cooling and solidifying the molten solution or the dispersed solution in a form of a block or a thin plate (flaky shape) by following conventional methods, and then conducting grinding and sizing.

The average diameter of the particles of the pharmaceutical preparation obtained by this method is generally about from 10 to 1400 μm and preferably about from 50 to 600 μm. The average particle diameter can be measured by generally known methods, such as sieving methods.

The method for preparing the medicinal composition of the present invention allows obtaining both a sustained-release preparation and a fast-release preparation. The type of preparation can be selected by controlling the size of particles of the preparation in consideration of the water-solubility of the active ingredient thereof.

Method B:

To the particles of the preparation obtained in method A described above, an excipient is added and, if necessary, a binder is further added. By following conventional methods, the blend is mixed, granulated and, optionally, compressed, thereby obtaining the composition of the present invention in the form of a powder, granules, dry-syrup, tablets, capsules, etc.

As an excipient, a wide range of publicly known types can be used, including mannitol, sorbitol, xylitol, maltitol, glucose, sucrose, lactose and like saccharides; cornstarch, potato starch and like starches; dibasic calcium phosphate anhydrous, calcium phosphate and like inorganic salts; crystalline cellulose, sodium carboxymethyl starch, dextrin, macrogol (for example, polyethylene glycol 6000, polyethylene glycol 4000, etc.), etc.

As a binder, various kinds of publicly known ones can be used including methylcellulose, hydroxypropyl cellulose, hydroxypropylmethyl cellulose, polyvinyl pyrrolidone, gelatin, gum arabic, polyvinyl alcohol, pullulan, macrogoal (for example, polyethylene glycol 6000, polyethylene glycol 4000, etc.), etc.

In preparing the composition of the present invention according to method B described above, in addition to an excipient, etc., it is possible to use various pharmaceutical carriers, such as disintegrators, lubricants, free-flow agents, sweetening agents, coloring agents, etc.

Examples of usable disintegrators include low-substituted hydroxypropyl cellulose, sodium carboxymethyl starch, croscarmellose sodium, carboxymethyl cellulose, crystalline cellulose, crospovidone, etc.

Examples of usable lubricants include magnesium stearate, calcium stearate, polyoxyl stearate, talc, sucrose esters of fatty acids, dimethylpolysiloxane, etc.

Examples of free-flow agents include light anhydrous silicic acid, etc.

Examples of coloring agents include coal-tar color, etc.

Furthermore, it is possible to add a flavor such as menthol to the composition of the present invention prepared by the above-mentioned methods.

The amounts of the excipient, binder, disintegrator, lubricant, free-flow agents, sweetening agent, coloring agent and flavor added are suitably selected depending on the pharmaceutically active substance used and the targeted pharmaceutical preparation.

The medicinal composition of the present invention (including sustained-release preparations and fast-release preparations of the present invention) comprises a low-melting-point substance, a pH-independent water-insoluble polymer and a pharmacologically active substance, wherein the pH-independent water-insoluble polymer and the pharmacologically active substance are each uniformly dispersed in each particle of the low-melting-point substance in a molecular state or a fine-particle state.

Specifically, the pH-independent water-insoluble polymer, such as ethylcellulose, and the pharmacologically active substance are not localized on or near the surfaces of the particles of the low-melting-point substance in a layered structure, but both the pH-independent water-insoluble polymer and the pharmacologically active substance are uniformly dispersed in each particle of the low-melting-point substance.

The medicinal composition of the present invention can also comprise a low-melting-point substance, a pH-independent water-insoluble polymer and a pharmacologically active substance, wherein the pharmacologically active substance is uniformly dispersed, in a molecular state or a fine-particle state, in each particle of the homogenized mixture or homogenized dispersion comprising the low-melting-point substance and the pH-independent water-insoluble polymer.

Specifically, the pharmacologically active substance is not localized on or near the surfaces of the particles of a matrix comprising the low-melting-point substance and the pH-independent water-insoluble polymer in a layered structure, but the pharmacologically active-substance is uniformly dispersed in each particle of the matrix.

Herein, "uniformly dispersed in a molecular state" means that a homogeneous solid (solid solution) of the mixture is formed, and "uniformly dispersed in a fine-particle state" means that the substance is dispersed in the matrix as fine particle without inconsistencies in density.

In this respect, the medicinal composition of the present invention has a structure fundamentally different from that of the preparation disclosed in Japanese Unexamined Patent Publication No. 1995-76517 in which small spherical particles comprising a molten wax-like substance and a pharmacologically active substance are covered with a hydrophobic substance and/or a water-insoluble polymer. Furthermore, the medical composition of the present invention also has a structure fundamentally different from that of the preparation disclosed in Japanese Unexamined Patent Publication No. 1996-143450 that is obtained by mixing a pharmacologically active substance that is easily soluble in water and a glycerin fatty acid ester, melting, granulating, adding a water-insoluble substance thereto, and further granulating and compressing.

In the medicinal composition of the present invention, the matrix comprising the low-melting-point substance and the pH-independent water-insoluble polymer is physically and chemically stable and the matrix carries the pharmacologically active substance in a uniformly dispersed manner. Therefore, the medicinal composition of the present invention exhibits excellent storage stability, and the release rate of the pharmacologically active substance does not readily change even over long-term storage.

BEST MODE FOR CARRYING OUT THE INVENTION

The present invention is explained in detail below with reference to Examples and Comparative Examples. Note that the components used below are as follows:

Component A (pharmacologically active substance):
 theophylline, average particle diameter of about 5 μm
Component B (low-melting-point substance):
 glycerin behenic acid ester, product name: Poem B-200, Riken Vitamin Co., Ltd.
Component C (pH-independent water-insoluble polymer):
 C-1: ethylcellulose, product name: Ethocel 7 cps Standard Premium, Dow Chemical Company
 C-2: aminoalkyl methacrylate copolymer RS, product name: Eudragit RS-PO, Rhöm GmbH & Co.KG

Examples 1 to 4

Glycerine behenic acid ester (component B) was melted by heating at about 140° C. and ethylcellulose (component C-1) or aminoalkyl methacrylate copolymer RS (component C-2) was added thereto and then melted. Theophylline (component A) having an average particle diameter of about 5 μm was added to the molten mixture and dispersed with stirring until it became homogeneous using a homomixer. The weight ratio of each component is shown in Table 1.

The resulting dispersions were subjected to spray cooling at the number of revolutions of about 2000 rpm using a rotary disc having a diameter of about 15 cm. The particles produced were sized by passing them through a sieve having openings of 500 μm, obtaining a sustained-release preparation of the present invention.

Comparative Example 1

A sustained-release preparation was prepared by following the same process of the above Examples except that component C was omitted.

TABLE 1

| Formula | Example 1 | Example 2 | Example 3 | Example 4 | Comparative Example 1 |
|---|---|---|---|---|---|
| Component A | 35 | 35 | 35 | 35 | 35 |
| Component B | 60 | 55 | 55 | 50 | 65 |
| C-1 | 5 | 10 | | | |
| C-2 | | | 10 | 15 | |
| Total (wt. %) | 100 | 100 | 100 | 100 | 100 |

Test Example 1

Figure 1:
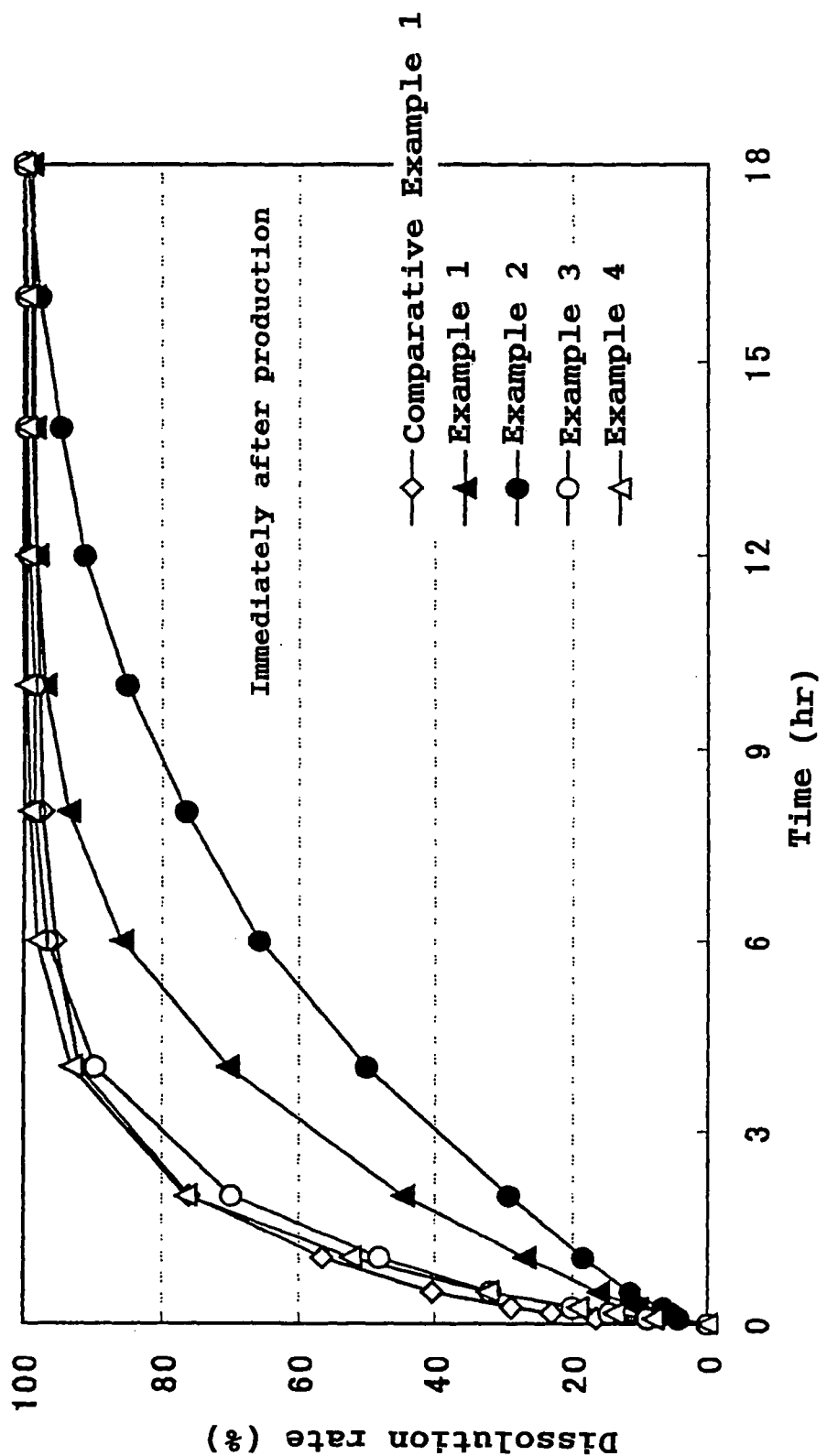
FIG. 1 is a graph showing the relationship between the elapsed time and the theophylline dissolution rate (%) of the pharmaceutical preparations obtained in Examples 1 to 4 and Comparative Example 1 examined immediately after production.

Each preparation immediately after being obtained in Examples 1 to 4 and Comparative Example 1 (amount equivalent to a theophylline content of 100 mg) was added to 900 ml of purified water, and the theophylline dissolution rate (%) was measured in accordance with the paddle method of the dissolution test of the Japanese Pharmacopoeia 13$^{th}$ division (paddle revolutions: 75 rpm). The relationship between the elapsed time after adding each preparation to the purified water and the dissolution rate was determined. FIG. 1 shows the results.

Figure 2:
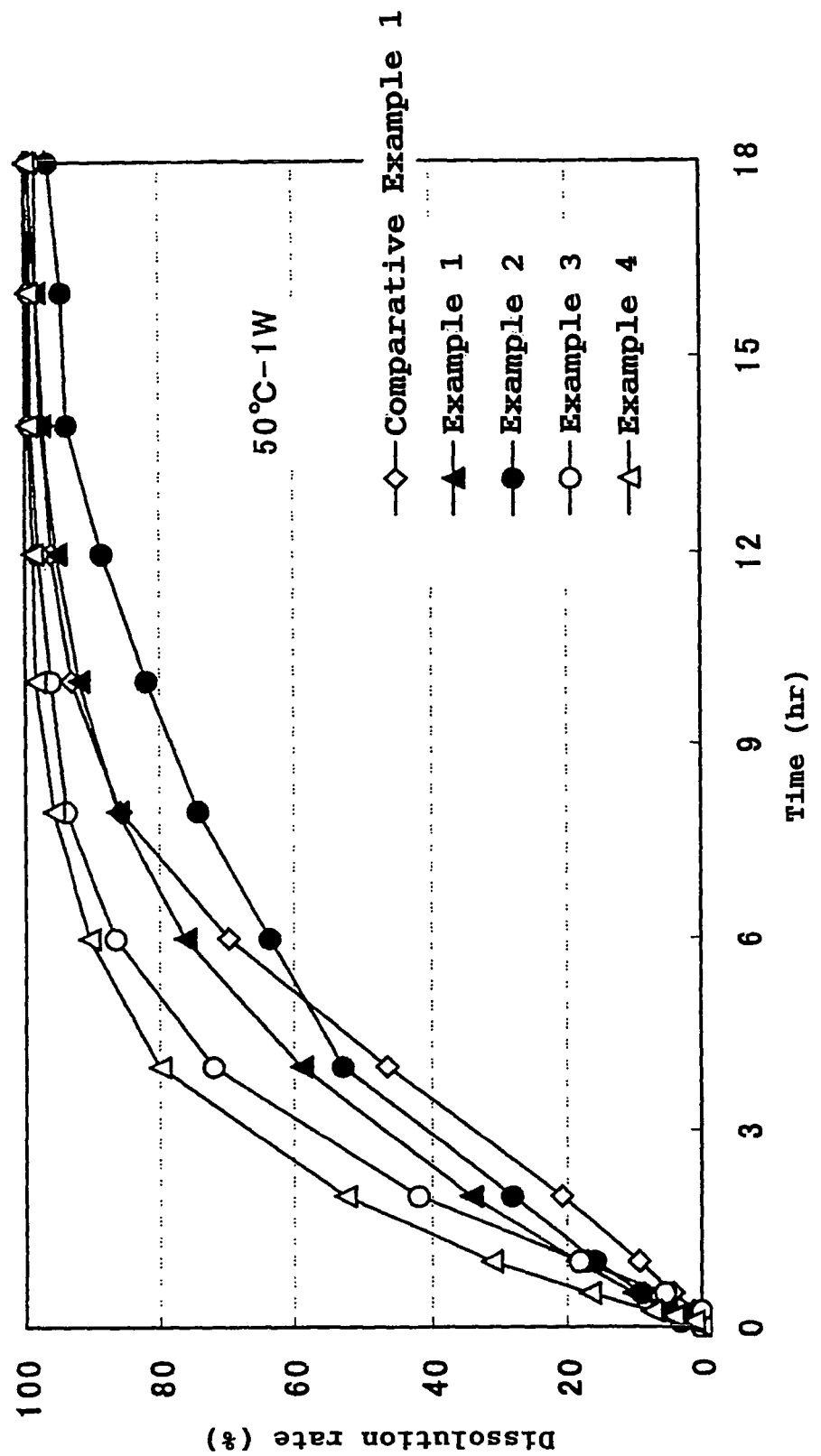
FIG. 2 is a graph showing the relationship between the elapsed time and the theophylline dissolution rate (%) of the pharmaceutical preparations obtained in Examples 1 to 4 and Comparative Example 1 examined after having been stored at 50° C. for a week.

After storing the preparations obtained in Examples 1 to 4 and Comparative Example 1 at 50° C. for one week, their theophylline dissolution rates (%) were measured by following the same process as described above. The relationship between the elapsed time after adding each preparation to the purified water and the dissolution rate was determined. FIG. 2 shows the results.

The following is clear from FIG. 1 and FIG. 2.

The sustained-release preparations of the present invention exhibit excellent storage stability and there is no significant difference in the theophylline dissolution rates between those examples examined immediately after production and having been stored at 50° C. for one week.

In contrast, the preparation obtained in Comparative Example 1 exhibited a significant difference in the theophylline dissolution rate between that examined immediately after production and after having been stored at 50° C. for one week. In other words, the preparation of Comparative Example 1 examined after having been stored at 50° C. for one week exhibited a significant lowered theophylline dissolution rate compared to that examined immediately after production.

Example 5

Glycerine behenic acid ester (component B) was melted by heating at about 140° C. Ethylcellulose (component C-1) was added thereto and then melted. Theophylline (component A) having an average particle diameter of about 10 μm was added to the molten mixture and dispersed or melted with stirring until it became homogeneous using a homomixer. The weight ratio of each component is shown in Table 2.

The obtained molten mixture was sprayed at the number of revolutions of 15000 rpm using a spray cooler having a diameter of 1.6 m (OC-16, manufactured by OKAWARA MFG CO., LTD. JAPAN) and then granulated. The obtained particles were sized by passing them through a sieve having openings of 355 μm, forming a fast-release preparation of the present invention.

Comparative Example 2

A fast-release preparation was prepared by following the same process of Example 5 except that component C was omitted.

TABLE 2

| Formula | Example 5 | Comparative Example 2 |
|---|---|---|
| Component A | 30 | 35 |
| Component B | 59.2 | 65 |
| C-1 | 10.8 | 0 |
| Total (wt. %) | 100 | 100 |

Test Example 2

Figure 3:
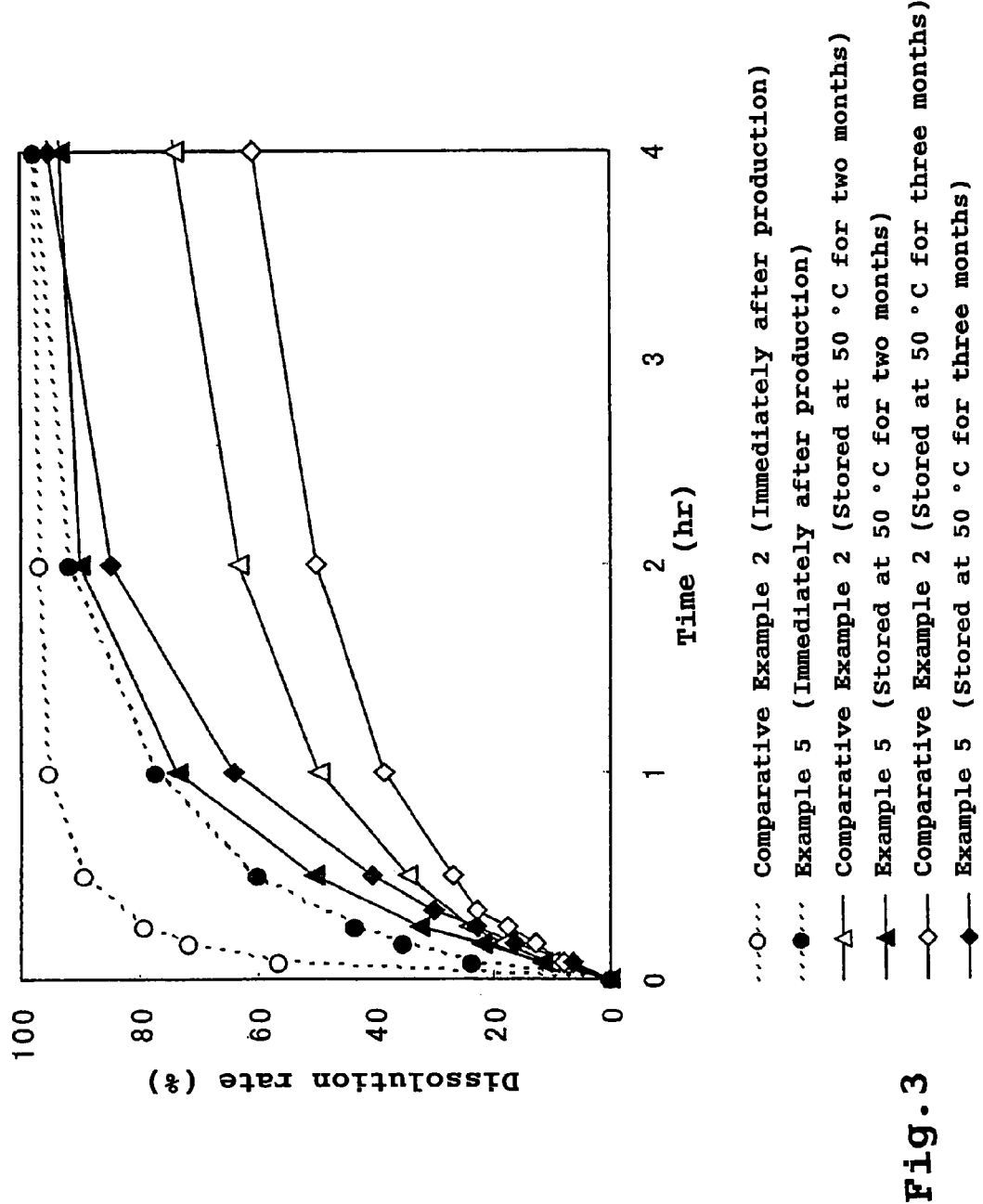
FIG. 3 is a graph showing the relationship between the elapsed time and the theophylline dissolution rate (%) of the pharmaceutical preparations obtained in Example 5 and Comparative Example 2 examined immediately after production or after having been stored at 50° C. for two months or for three months.

Each preparation immediately after being obtained in Example 5 and Comparative Example 2 (amount equivalent to a theophylline content of 100 mg) was added to 900 ml of purified water, and its theophylline dissolution rate (%) was measured in accordance with the paddle method of the dissolution test of the Japanese Pharmacopoeia 13$^{th}$ division (paddle revolutions: 75 rpm). The relationship between the elapsed time after adding the preparations to the purified water and the dissolution rate was determined. FIG. 3 shows the results.

After storing the preparations obtained in Example 5 and Comparative Example 2 at 50° C. for two months or three months, their theophylline dissolution rates (%) were measured by following the same process as described above. The relationship between the elapsed time after adding the preparations to the purified water and the dissolution rate was determined. The results are also shown in FIG. 3.

Focusing on the theophylline dissolution rate (%) after a lapse of one hour in FIG. 3, the change in the theophylline dissolution rate (%) of the preparations examined after having been stored at 50° C. for two months or three months compared to those examined immediately after production was reviewed. In other words, when the theophylline dissolution rates (%) of the preparations examined immediately after production were normalized as 100 (base value), with this value as a base, the theophylline dissolution rates (%) of the preparations examined after having been stored at 50° C. for two months or three months were likewise expressed numerically. These numerical values were determined as the change rate (%) of theophylline dissolution of after elapse of one hour. The results are shown in FIG. 3.

TABLE 3

| | Change rate (%) of dissolution amount of theophylline after one hour | | |
|---|---|---|---|
| | Immediately after production | Stored at 50° C. for two months | Stored at 50° C. for three months |
| Example 5 | 100 | 95 | 83 |
| Comparative Example 2 | 100 | 51 | 40 |

The following is clear from FIG. 3 and Table 3.

The fast-release preparation of the present invention exhibits excellent storage stability and there is no significant difference between the preparation immediately after production and the preparation after having been stored at 50° C. for two months or three months, except a slight decrease in the dissolution rate.

In contrast, the preparation obtained in Comparative Example 2 shows a significant difference in the theophylline dissolution rate when examined immediately after production and when examined after having been stored at 50° C. for two or three months. In other words, in Comparative Example 2, the theophylline dissolution rates of the preparations examined after having been stored at 50° C. for two or three months were significantly lowered as compared to that of the preparation examined immediately after production.

The medicinal composition of the present invention exhibits excellent storage stability and has the advantage that even after the preparation has been stored for a long time, the release rate of the pharmacologically active substance does not significantly change. Therefore, the medicinal composition of the present invention can provide medicines with high quality because it can be stored for a relatively long time and maintain a stable release rate of the pharmacologically active substance.

Furthermore, because organic solvents are not used when preparing the composition of the present invention, it does not render problems such as adverse effects on workers' health, environmental pollution and residues in the resulting preparation.

The invention claimed is:
1. A medicinal composition consisting essentially of a pharmacologically active substance, a low-melting-point substance and a pH-independent water-insoluble polymer, which is prepared by spraying a liquid substance obtained by dissolving or dispersing a pharmacologically active substance in a molten mixture containing a low-melting-point substance and a pH-independent water-insoluble polymer, and cooling the sprayed liquid substance,
   wherein the medicinal composition is a sustained release preparation or a fast release preparation,
   the low-melting-point substance is a glycerin behenic acid ester or a glycerin stearic acid ester, and
   the pharmacologically active substance is at least one member selected from the group consisting of theophylline, cilostazol, grepafloxacin, carteolol, procaterol, rebamipide and aripiprazole,
   the pH-independent water-insoluble polymer is a single substance or a mixture of two or more substances selected from the group consisting of ethylcellulose, aminoalkyl methacrylate copolymer RS, aminoalkyl methacrylate copolymer RL, cellulose acetate, cellulose acetate butyrate, and cellulose acetate propionate, and which contains the pH-independent water-insoluble polymer in the proportion of from 8.3 to 45 wt. % relative to the low-melting-point substance.

2. The medicinal composition according to claim 1, which contains the low-melting-point substance in the proportion of from 50 to $1\times10^5$ wt. % relative to the pharmacologically active substance.

3. The medicinal composition according to claim 1, which is composed of particles having an average particle diameter of about from 10 to 1400 μm.

4. A method for preparing a medicinal composition comprising the steps of:
  obtaining a molten mixture by dissolving (melting) or dispersing a pH-independent water-insoluble polymer in a molten low-melting-point substance,
  wherein the low-melting-point substance is a glycerin behenic acid ester or a glycerin stearic acid ester,
  the pH-independent water-insoluble polymer is a single substance or a mixture of two or more substances selected from the group consisting of ethylcellulose, aminoalkyl methacrylate copolymer RS, aminoalkyl methacrylate copolymer RL, cellulose acetate, cellulose acetate butyrate, and cellulose acetate propionate, and
  the pH-independent water-insoluble polymer is employed in the proportion of from 8.3 to 45 wt. % relative to the low-melting-point substance;
  obtaining a liquid substance by dissolving or dispersing a pharmacologically active substance in the molten mixture, wherein the pharmacologically active substance is at least one member selected from the group consisting of theophylline, cilostazol, grepafloxacin, carteolol, procaterol, rebamipide and aripiprazole; and
  obtaining particles by spraying and then cooling the liquid substance.

5. The method for preparing a medicinal composition according to claim 4, wherein the medicinal composition is a sustained-release preparation or a fast-release preparation.

* * * * *